United States Patent [19]

Bucke et al.

[11] 4,359,531
[45] Nov. 16, 1982

[54] PRODUCTION OF ISOMALTULOSE

[75] Inventors: Christopher Bucke; Peter S. J. Cheetham, both of Reading, England

[73] Assignee: Talres Development (N.A.) N.V., Curacao, Netherlands Antilles

[21] Appl. No.: 201,462

[22] Filed: Oct. 28, 1980

[30] Foreign Application Priority Data

Nov. 7, 1979 [GB] United Kingdom ................ 7938563

[51] Int. Cl.³ .................... C12P 19/18; C12P 19/12; C12R 1/425; C12N 11/10
[52] U.S. Cl. ..................................... 435/97; 435/100; 435/178; 435/847; 435/880; 426/536; 426/658
[58] Field of Search ............... 435/100, 174, 847, 880, 435/97, 182, 178; 426/536, 658

[56] References Cited

FOREIGN PATENT DOCUMENTS

| 1099 | 3/1979 | European Pat. Off. ............ 435/100 |
| 1049800 | 11/1959 | Fed. Rep. of Germany . |
| 1429334 | 3/1976 | United Kingdom . |

OTHER PUBLICATIONS

Kolarik, et al, Glueose Isomerase Cells Entrapped in Cellulose Acetates, *Immobilized Enzymes in Food and Microbial Processes* 1973 Plenum Press, NY 71–83.
Kierstan, The SImmobilization of Microbial cells, Subcellular organelles, and enzymes in calcium alginate gels, 1977 *Chem. Abs.*, vol. 86, 188.
Cheetham Physical Studies on Cell Immobilization using Calcium Alginate Gels, *Biotechnology and Bioengineering* vol. 21, No. 12, 1979.
Stodola et al, A New Disaccharide Produced by Leuconostoc Mesenteroides, *J. Amer. Chem. Soc.* 74:3202 (1952).
Stodola, et al, The Preparation, Properties and Structure of the Disaccharide Leucrose, *J. Amer. Chem Soc.* 78:2514 (1956).
Sharpe, et al, Formation of Isomaltulose in Enzymatic Dextran synthesis *J. Org. Chem.* 25:1062 (1960).
Chibata et al, Production of L-Aspartic Acid by Microbial Cells Entrapped in Polyacrylamide Gels, *Methods in Enz* 44:739 (1976).

*Primary Examiner*—Thomas G. Wiseman
*Assistant Examiner*—Kathleen S. McCowin
*Attorney, Agent, or Firm*—Ostrolenk, Faber, Gerb & Soffen

[57] ABSTRACT

Isomaltulose is produced by a process in which at least the isomaltulose-forming enzyme system of an isomaltulose-forming micro-organism genus Erwinia is immobilized on calcium alginate gel and then the immobilized enzyme system is contacted with a sucrose solution to convert at least part of the sucrose to isomaltulose.

12 Claims, 4 Drawing Figures

PRODUCTION OF ISOMALTULOSE

The present invention relates to the production of isomaltulose. More particularly, this invention relates to the production of isomaltulose from sucrose by an enzymatic conversion.

Isomaltulose is a reducing disaccharide which is otherwise known as palatinose. It has the structure and is more systematically known as 6-O-(α-D-glucopyranosyl)-D-fructofuranose.

Historically, isomaltulose was first mentioned in a 1952 article (J.Amer.Chem.Soc. 74,3202 (1952)) as a by-product of a fermenting micro-organism, *Leuconostoc mesenteroides*. Subsequent work published in 1956 and 1960 (respectively, J.Amer.Chem.Soc. 78, 2514 (1956) and J.Org.Chem. 25, 1062 (1960)) confirmed the formation of isomaltulose as a by-product of dextran synthesis from sucrose by *L. mesenteroides*.

German Patentschrift No. 1049800 (published 1959) in the name of the Suddeutsche Zucker-Aktiengesellschaft describes how isomaltulose may be obtained from sucrose by a microbiological process using *Protaminobacter rubrum*. It is now known that other bacteria may be used to effect the conversion of sucrose to isomaltulose, and in their UK Patent Specification No. 1,429,334 (which corresponds to German Patentschrift No. 2217628), the same company mentions that *Serratia plymuthica* is suitable.

The UK Patent Specification No. 1,429,334 is primarily directed to the preparation of isomaltitol (α-D-glucopyranosyl-1,6-sorbitol) from isomaltulose by a catalytic hydrogenation. In practice, the hydrogenation gives a mixture that also contains α-D-glucopyranosyl-1,6-mannitol; this mixture is available as a low calorie sweetener under the trade name 'Palatinit'.

Proceeding from a mention of the German Patentschrift No. 1049800, the UK Patent Specification No. 1,429,334 discloses that the conversion of saccharose (ie. sucrose) to isomaltulose is suitably effected by a fermentation using a sucrose solution of 15% to 40% wt/wt, preferably 20 to 25% wt/wt sucrose. Vigorous stirring and continuous passage of air are used. The UK Specification further states that the conversion can be effected batch-wise or continuously and has a respective example for both techniques. After the fermentation, the isomaltulose solution is separated off and can be crystallized following filtration and ion-exchange chromatography.

In their European Patent Specification No. 0001099 published on March 21, 1979, the Bayer Aktiengesellschaft describe a process for continuous fermentation of micro-organisms, e.g. *Protaminobacter rubrum* or *Serratia plymuthica*, with simultaneous conversion of sucrose to isomaltulose. They observe that they have now found that the cultivation of isomaltulose-forming micro-organisms can be carried out continuously with simultaneous conversion of sucrose into isomaltulose, and assert that it was surprising and unexpected that isomaltulose-forming micro-organisms might simultaneously convert sucrose to isomaltulose during growth in sucrose-containing plant juices.

The sucrose-containing solution is specified as a thin juice/thick juice and/or thin juice/clarified product mix from a sugar factory and having a dry substance content of 5 to 30%, preferably 20 to 27%, the dry substance being 90 to 98% sucrose. Apart from *Protaminobacter rubrum* and *Serratia plymuthica*, the European Patent Specification No. 0001099 refers to the possibility of using *Serratia marscescens*, *Erwinia carotovora* or *Leuconostoc mesentheroides* as the isomaltulose-forming micro-organism.

We have been investigating ways in which the conversion of sucrose to isomaltulose can be effected in a more efficient manner and have been considering possible new uses to which isomaltulose can be put.

According to the present invention, we provide a process for the production of isomaltulose from a sucrose solution which uses the immobilized isomaltulose-forming enzyme system of an isomaltulose-forming micro-organism.

The present process is not one of bacterial aerobic fermentation as disclosed in the prior art, but instead employs immobilization to support the enzyme or enzymes which comprise the enzyme system involved in the conversion of sucrose to isomaltulose.

The enzyme system can be used after extraction from the isomaltulose-forming micro-organism, though extraction is not necessary. Thus, for instance, it is possible to use the whole or disrupted cells of the micro-organism, with the cells acting as a vehicle or carrier for the enzyme system.

Some division of whole cells may occur post-immobilization, but we greatly prefer that the immobilization technique and other process variables are so chosen that division is absent or at a minimum. In the preferred process, no steps are taken to maintain viability of the cells: it is usually the case that no cell division occurs when an attempt is made to grow the cells after extended use in the preferred process.

More generally, it is a feature of the way in which the process is best performed that the sucrose solution is nutritionally deficient lacking, one or more nutrients required for growth of the isomaltulose-forming micro-organism. In this way it is possible to achieve the desired minimization of the cell division when using immobilized whole cells to provide the enzyme system. In turn, the absence of nutrients can mean a purer product and reduce the risk of growth of any infecting micro-organism.

The enzyme system responsible for forming isomaltulose can be extracted from cells of the micro-organism by conventional techniques, for example by a solvent extraction. To facilitate extraction one can use ancilliary procedures, for example disrupting the cells, or osmotic shocking. From our experiments on *Erwinia rhapontici* (the preferred isomaltulose-forming micro-organism for the present process), it appears that the enzyme system is located in the periplasmic space of the cells, and that the enzyme system is a sucrose-specific glucotransferase utilizing only the fructose derived from sucrose and not utilizing free fructose or fructose combined in other molecules. The extracted enzyme system can if desired by purified before use, for example by electrophoresis.

Various techniques known in themselves can be used for immobilization of the enzyme system of the isomaltulose-forming micro-organism. For example, it is possible to use entrapment within a gel. Other immobilization techniques can be used as alternatives to entrapment. For instance, the cells can be physically adsorbed on an inert support; they can be covalently coupled to an inert support; or they can be aggregated by use of a cross-linking agent.

Of the immobilization techniques we have tried, we prefer entrapment in a gel, particularly since it is suited to immobilization of an enzymatically active extract of the cells as well as the whole or disrupted cells. Suitable gel materials include alginate, polyacrylamide, agar, xanthan gum/locust bean gum, kappa-carrageenan or kappa-carrageenan/locust bean gum, collagen, or cellulose acetate.

Of these gel materials, we find an alginate gel, in particular a calcium alginate gel, gives best results. Other alginate gels can be used, such as those formed with other group II metals, but we much prefer calcium alginate. We especially prefer the immobilization of whole cells in a calcium alginate gel. In this way the cells are trapped in an inert, three-dimensional polymer network with relatively large interstitial spaces in the gel.

For a calcium alginate gel, the rate of inward diffusion of sucrose is high and also most of the intra-gel space can be reached by the sucrose. Moreover, the rate of outward leakage of whole cells and protein is very low and when subjected to pressure, the gel slightly deforms but does not compress to any appreciable extent. An additional advantage is the exceptional and surprising stability of the isomaltulose-forming activity of the immobilized whole cells; the half-life of the activity of the cells entrapped in calcium alginate gel approaches 10,000 hours, with 8,500 hours being a typical figure, whereas the longest half-life under comparable circumstances for the other immobilization procedures we have tried is under 1,000 hours. In contrast to most of the usual immobilization techniques, immobilization in alginate gel typically results in no appreciable loss of activity.

For immobilization of the enzyme system (in itself or as a whole or disrupted cells) in alginate gel, we prefer first to mix the enzyme system with an aqueous solution of a soluble alginate, for example sodium alginate. In a preferred process, this will involve slurrying whole cells with the soluble alginate. The concentration of cells in the slurry is in no way critical to the success of the present process, but by trying various concentrations an optimum can readily be found for a particular system. Typically the concentration of cells is between 1 and 90% wet weight/volume (ww/v), although preferably it is from 10 to 40% ww/v, more preferably about 20% ww/v. Equally, the concentration of soluble alginate is not critical. A particularly suitable concentrations for use with whole cells or other forms of the enzyme system is between 1 and 10% w/v, more especially about 5% w/v.

The resultant alginate mixture is then metered into a solution of a metal salt with which the soluble alginate forms a gel. As mentioned, the preferred gel is calcium alginate, and suitable salts then include calcium chloride. In particular, we prefer to use a calcium chloride solution whose molarity is from 0.01 to 1.0 M, more preferably from 0.05 to 0.5 M, most preferably around 0.1 M. The metal salt solution is preferably at 15°–40° C., more especially around 30° C., as the mixture is metered in, and it is also advantageous if the solution is stirred. The stability of the immobilized enzyme system is enhanced if the metal salt solution further contains some dissolved sucrose, eg 5 to 40% (w/v) sucrose, preferably about 20% (w/v) sucrose.

By metering the slurry or other alginate mixture as discrete droplets, it is a simple matter to produce spherical pellets of gel entrapping the enzyme system. The pellet size can be varied, but for ease of handling and for efficient mass transfer properties in use, it is preferred to be about 3 to 5 mm in diameter. However, the size and shape is of limited consequence, and it is readily possible to immobilize the enzyme system in a block of gel (which is then divided for use), in a rope of gel (which for use can be wound on a former or cut into sections), or in microfibrous particles (by using high shear conditions upon metering in the alginate mixture).

Similar techniques can be used for immobilizing the enzyme system in other gel systems. Procedures for forming gelled products are available in the literature, and it is a simple matter to adapt them to the present purposes. By way of non-limiting examples, we mention that we have successfully used the following to immobilize the enzyme system as immobilized whole cells:

(i) Kappa-carrageenan, or Kappa-carrageenan/locust bean gum, using the same procedure as for alginate except that the most preferred solution into which the cell slurry was extruded was a mixture of 1 M $CaCl_2$ and 1 M KCl at 20° C.

(ii) Agar, by boiling 3% w/v agar in deionized water, cooling the resultant gel to 50° C., adding the slurry of cells, and extruding the suspension obtained drop-wise in to ice-cold water;

(iii) Xanthan/locust bean gum, using the same procedure as for agar with the exceptions that the gum was heated only to 80° C. and the gel was cooled to 60° C. before adding the cells; and (iv) Polyacrylamide, using the method of Chibata et al (Methods in Enzymology, 44, (1976) 739).

It is not essential to use a gel to immobilize the whole or disrupted cells of the isomaltulose-producing microorganism. Again by way of non-limiting examples, we mention that we have successfully adsorbed whole cells on DEAE-cellulose. 2 g of cells were mixed with 10 ml of a very thick aqueous slurry of DEAE-cellulose adjusted to pH 7 with tris(hydroxymethyl)aminomethane hydrochloride salt, ie tris-HCl. The slurry was held at room temperature for 30 minutes and was then ready for use.

Moreover, we have immobilized cells by cross-linking. This was effected by reacting 2 g of cells suspended in 10 ml of deionized water with a cross-linking agent, 10 ml of 25% v/v glutaraldehyde.

Immobilization on bone char has also successfully been performed, using 2 g of cells and 2 g of unsieved bone char which were suspended in 10 ml of deionized water for 30 minutes. Thereafter a solution of 150 mg tannic acid and 130 mg of glutaraldehyde in 2.2 ml of acetone was added. The mixture was held at room temperature to complete the immobilization.

It will be appreciated from the foregoing discussion that the immobilization of the enzyme system can be effected in ways which do not use a gel system. When using physical adsorption on an inert support, it is preferred to form a mono- or duo-layer of adsorbed cells. A similar preference for mono- or duo-layers applies when using covalent coupling to an inert support, while when forming aggregates with a cross-linking agent it is preferred that the degree of aggregation is such as to render the aggregates just visible.

As a generality, when isomaltulose-forming enzyme systems are immobilized by methods other than entrapment in calcium alginate gel, the retention of activity and the stability of the activity is usually less. However, the other modes of immobilization often have different characteristics which may make them desirable. Thus, as an example, adsorption of the cells onto DEAE-cellulose has the advantage that the liquor obtained after the conversion is typically crystal clear-seemingly any impurities are adsorbed by the DEAE-cellulose. More generally, the alternative techniques of immobilization may be chosen to suit particular circumstances and are of use in the present invention.

Immobilization of disrupted cells or solvent extracts of the enzyme system avoids all possibility of cell division occurring during use, thus preventing breakdown of pellets and blockage of pores which is sometimes encountered when immobilized whole cells divide within calcium alginate gel pellets. Moreover, with immobilized disrupted cells or solvent extracts the initial activity is high, reflecting the absence of an intact cell wall membrane which might act as a carrier to diffusion of sucrose and isomaltulose. Disruption can be carried out by ball-milling or other treatment of whole cells.

The source of the enzyme system employed in the immobilization is preferably an isomaltulose-producing micro-organism of the genus Erwinia. Bacteria of other genera can be utilized, such as *Serratia plymuthica* or *Protaminobacter rubrum*, but the former is possibly a human pathogen and the latter tends to produce an unwanted low molecular weight red pigment. Mutants, variants and other artifacts of the naturally occurring bacteria can be used if desired. For example, mutants can be induced by chemical or physical means.

Of the species belonging to the genus Erwinia, *E. rhapontici* is particularly preferred. Especially suitable strains of *E. rhapontici* include those deposited in Britain at the National Collection of Plant Pathogenic Bacteria under the Accession Numbers NCPPB 1578, NCPPB 139 and NCPPB 1739. The strain NCPPB 1578 is also deposited at the American Type Culture Collection under the Accession Number ATCC 29283. All NCPPB strains mentioned in this specification are listed in the 1st edition of the "Catalogue of Cultures in the National Collection of Plant Pathogenic Bacteria" published in 1977 by the United Kingdom Ministry of Agriculture, Food and Fisheries and are available to the public.

The strains NCPPB 1578, 139 and 1739 are exceptionally promising, having a higher product specificity, initial activity, and stability when compared by us with other strains of Erwinia or with strains of other genera.

A process in accordance with the present invention is preferably carried out as a continuous process, suitably by loading the immobilized enzyme system into a column and passing the substrate sucrose as a solution through the column. In a preferred arrangement, several columns are employed in parallel, for example on a carousel. The column size can be chosen as desired, but is conveniently from 20 ml upwards. Some carbon dioxide is normally formed during the conversion of the sucrose to isomaltulose when using immobilized whole cells, and it is easier to displace this carbon dioxide if the liquid is passing up-wards through the column. Upward passage of the liquid can also help to fluidize the bed of immobilized enzyme system and avoids compaction such as might occur with downward passage.

Whereas the known processes for producing isomaltulose by fermentation are preferably carried out using a sucrose solution of around 25% by weight sucrose, the present process surprisingly gives better results if operated at higher sucrose concentrations, for example using as substrate a sucrose solution containing at least 30%, preferably at least 40% and more preferably at least 50% (w/v) of sucrose.

The stability (measured as half-life) of the isomaltulose-synthesising enzyme system in the immobilized cells increases with increase in the sucrose concentration, as does the concentration of isomaltulose in the converted liquid.

These effects are quite marked, and are illustrated graphically in FIGS. 1 and 2 of the accompanying drawings which are based on experimental data obtained using calcium alginate pellets of immobilized *E. rhapontici* NCPPB 1739. In the drawings.

Figure 1:
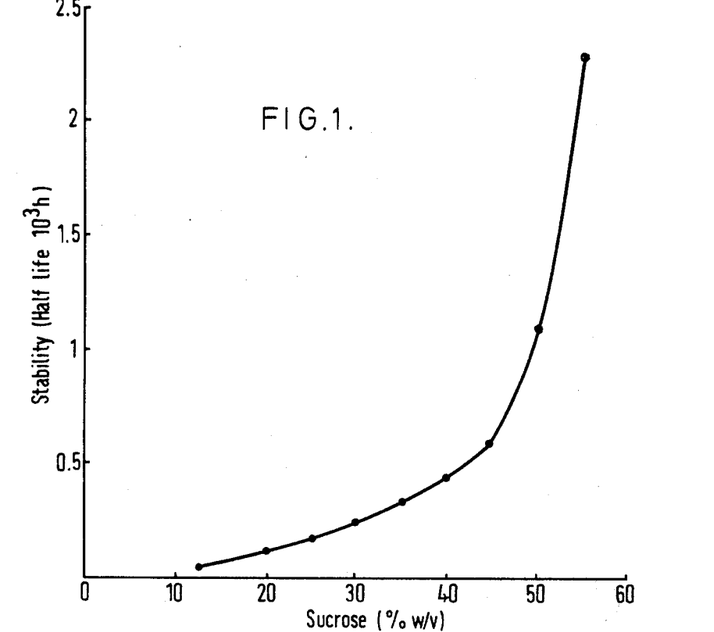
FIG. 1 shows the variation in stability of the immobilized cells with respect to the concentration of the sucrose solution.
Figure 2:
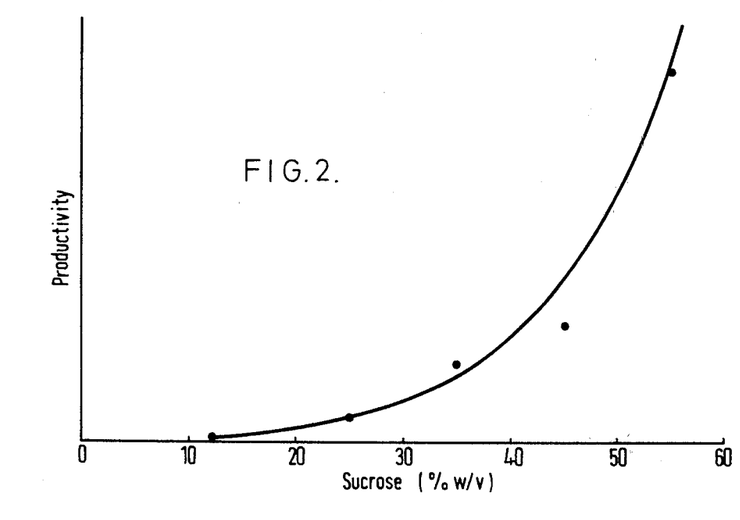
FIG. 2 shows the effect of the sucrose concentration on the productivity of the immobilized cells.

Particularly as the sucrose concentration rises above 30 to 40%, the stability and productivity increase by a remarkably greater amount. This effect seems chiefly to be a property of the immobilized isomaltulose-forming enzyme system, rather than of the immobilization technique. This said, an immobilization technique which employs calcium alginate usually gives the better stability.

Moreover, a high sucrose concentration tends to inhibit division of immobilized cells and to prevent microbial contamination, while at the same time making it easier to recover the product and decreasing the volume of liquid to be processed.

There are thus considerable advantages now obtainable in using as high a sucrose concentration as is convenient, and in practice the only limitation is usually the viscosity of the solution. We find that in most circumstances, the upper viscosity limit is between 100 cp and 1000 cp, typically 500 cp.

For the preferred process employing cells entrapped in calcium alginate gel pellets, the sucrose concentration in the starting material is conveniently about 55% w/v.

The substrate need not be a solution of pure sucrose; for example up to 15% v/v of molasses can be incorporated instead of sucrose, and the process can utilize recovery house material or "affination syrup", these being two types of impure sugar stream found in conventional sugar refineries.

The conversion of sucrose to isomaltulose in accordance with the present invention is preferably performed at 15° to 40° C., more preferably 20° to 35° C., with a temperature of about 30° C. being particularly suitable.

The pH of the sucrose solution is not particularly critical, preferably being from 5 to 9, more preferably around 7. The conversion to isomaltulose normally results in the generation of some acid, but in practice it is usually unnecessary to take steps to maintain the pH to within the range of pH 5 to 9. In any case, acid generation is usually reduced as the substrate concentration is increased.

The present process can be operated so as to achieve a controlled degree of conversion of sucrose to isomaltulose and any accompanying products. As the residence time increases of the sucrose in contact with the immobilized enzyme system, so the degree of conversion increases towards the practical maximum (typically between 85 and 100% conversion of sucrose to products). However, the maximum productivity is not necessarily achieved at the highest degree of conversion because the greater throughput and higher activity resulting from a shorter residence time may compensate for not operating at maximum conversion.

Thus, in practice, we find that the maximum productivity is obtained by operating at less than maximum conversion, usually at between 70 and 95% conversion to products. We prefer to operate the present process at or nearly at the degree of conversion required for maximum productivity. The conversion required to achieve greatest productivity can readily be found by systematic experimentation. To give one example, we find that for calcium alginate pellets of immobilized Erwinia cells there is usually a maximum in productivity when operating at between 80 and 90% conversion.

Figure 3:
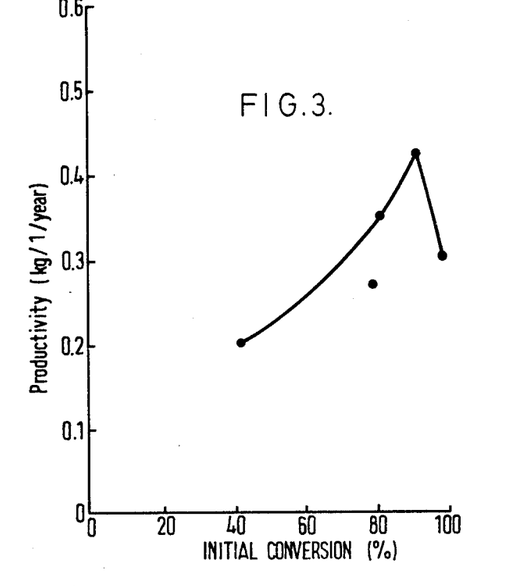

The existence of this maximum in productivity is illustrated graphically in FIG. 3 of the accompanying drawings which is based on experimental data obtained using calcium alginate pellets of immobilized *E. rhapontici* NCPPB 1739.

FIG. 3 shows the variation in productivity of the immobilized cells with respect to the initial percentage conversion (that is, percentage conversion as extrapolated back to time zero).

There is a marked peak in productivity at around 85 to 90% conversion of sucrose to isomaltulose and accompanying products.

Figure 4:
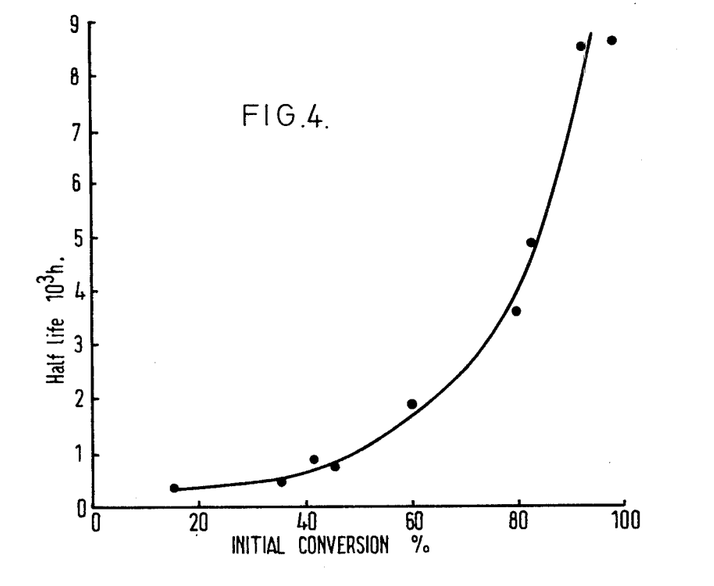

The degree of conversion of sucrose to products also has a remarkable effect on the stability of the isomaltulose-forming enzyme system of the immobilized cells. Our experiments show that the stability can increase exponentially with the degree of conversion of a concentrated sucrose solution. This effect is illustrated graphically in FIG. 4 of the accompanying drawings which is based on experimental data obtained using calcium alginate pellets of immobilized *E. rhapontici NCPPB* 1739. In the drawings;

FIG. 4 shows the variation in half-life of the immobilized cells with respect to the initial percentage conversion.

The data for FIG. 4 were obtained for conversion of a 55% sucrose solution. The stability increases exponentially to a value of around 8500 hours at 90% conversion. This dramatic result is most unexpected and again illustrates the advantages obtainable with the present invention.

In general, the process of this invention gives a solution which contains isomaltulose and other saccharides, along with unconverted sucrose. We have not yet been able to isolate all the various impurities, but have determined the presence of sucrose, glucose and fructose and we suspect the presence of other saccharides.

After the isomaltulose has been formed, it can be crystallized or otherwise purified, though this is not essential to the invention.

For crystallization, we prefer to concentrate the solution to a concentration of 60% (w/v) or more preferably, about 65% or 70% (w/v), and then seed and cool the solution with stirring to 20° C. The concentration is preferably performed by evaporation carried out at no higher than 65° C., thereby minimizing colour formation. Seeding of the concentrated solution encourages growth of small crystals, though large crystals can be grown if desired. There is no difficulty in obtaining a primary crop of crystals comprising 90% isomaltulose, and successive crystallizations will raise the purity to 100%.

Crystals of isomaltulose can also be obtained by addition of ethanol or other precipitating agent (for example, sucrose) to the converted solution. In this way crystals are rapidly produced in good yield, though the purity is often less than that achieved with the concentration crystallization procedure described in the preceding paragraph. The crystals formed by addition of ethanol typically contain about 80% isomaltulose, with sucrose as the main impurity.

When an impure sucrose solution, such as affination syrup, is converted, the crystals obtained by the concentration-crystallization procedure are usually light brown in colour and relatively impure.

Up to 95% or more of the total isomaltulose present in the product liquid can readily be recovered as crystals, the actual figure depending on the crystallization technique and number of successive crystallizations which are employed. Comminution of the crystals gives a free-flowing powder which is principally isomaltulose.

As an alternative to purification by crystallization, the product liquid can be purified by contact with a basic exchange resin such as Amberlite IRA-68 (to remove acids, Amberlite being a registered trade mark and with immobilized yeast cells to remove glucose, fructose and sucrose). Moreover, freeze-drying or other techniques can be used to produce a solid product.

We have determined that isomaltulose has some physical properties similar to those of sucrose though it does have much reduced sweetness (37% that of sucrose sweetness at 7% w/v in water). Surprisingly, we have also found that isomaltulose has less readily quantifiable properties which make it especially suited for use in place of sucrose as an ingredient in the preparation of products for human or animal consumption.

The use of isomaltulose in place of sucrose in such products is the subject of our separate patent application Ser. No. 201,463 also claiming a priority date of Nov. 7, 1979. As described in the specification of that other patent application, isomaltulose is especially useful in preparing cooked foods, giving bulk, structure, texture and other desired effects. Flavours are often accentuated when using isomaltulose in place of sucrose, and baked products usually assume a darker, richer colour. In the other specification we give examples which include toffees, biscuits, puddings, cakes, and jam.

For the use in foods and related products, one can use crystallized isomaltulose provided by the invention—the isomaltulose need not be pure, and for some uses the uncrystallized impure product can be employed.

The present invention is illustrated by the following non-limiting details of examples we have carried out. In the following, a weight in grams of cells refers to a wet weight (ww); an approximate conversion to dry weight can be made by dividing by 5. Activities of cells are expressed per gram of wet cells.

EXAMPLE 1

Cells from a culture of *Erwinia rhapontici* (NCPPB 1578, ATCC 29283) were diluted with 10 ml of phosphate-buffered saline. 0.10 ml aliquots of the resultant suspension were used to inoculate 200 ml aliquots of growth medium in 500 ml sterilized, baffled shake flasks. The medium was as shown in the following Table 1:

TABLE 1
Growth Medium

| Component | Amount (g/l distilled water) |
| --- | --- |
| Sucrose | 40 |
| peptone (digested casein) | 10 |
| beef extract | 4 |

The inoculated flasks were shaken at 120 oscillations per minute at 30° C. for 70 hours and then harvested. The cells were harvested in the stationary growth phase in this instance, but equally can be harvested in the logarithmic growth phase or the death phase. The cells were centrifuged at 15,000 'g' for 10 minutes at 30° C., thereby giving about 1 g packed wet cells per 100 ml of medium. (When larger volumes of incubated medium were to be processed, a continuous action centrifuge rotor was used with the medium being pumped through at 100 ml/min).

The harvested packed cells were then immediately suspended in a solution of sodium alginate (5% dry w/v) in deionised water so as to form a 20% wet w/v suspension of cells. The cell suspension was then extruded dropwise from a height of 10 cm into a stirred solution of calcium chloride (0.1 M) maintained at 30° C. and also containing 15% w/v sucrose which served to stabilize the isomaltulose-synthesizing activity of the cells. The resulting pellets were stirred for 1 hour and then packed into a jacketed column (30 cm tall, 5 cm diameter).

A solution of sucrose 55% (w/v) in deionised water was prepared and adjusted to pH 7.0 with 1.0 M NaOH. The sucrose solution was pumped up the column, which was maintained at 30° C. With the sucrose flow rate at approximately 0.01 empty column volumes/hour (ecv/h), conversion of sucrose to isomaltulose and other products approached equilibrium.

A steady state was reached after 24 h. By this time, the activity of the immobilized cells was about 0.2 g product/g wet cells/h. The stability of the cells, expressed as a half-life, was about 1 year. When the sucrose flow rate was increased so as to reduce the conversion to 80%, the activity was about 0.325 g product/g wet cells/h.

The column eluate was collected, evaporated to about 70% (w/v) at 60° C., and then allowed to cool, or was force cooled while being agitated, thereby giving small white crystals. In practice, crystals could be recovered more quickly by seeding the cooled solution with a small quantity of dry isomaltulose. The crystals were collected by filtration of centrifugation and dried at 40° C. and 700 mm Hg in a vacuum oven. The product was analysed and then assayed. The crystals were 94.5% isomaltulose with one molecule of water of crystallization per molecule of isomaltulose, the remainder being other sugars. Recrystallization three times gave pure isomaltulose.

Typically, if the substrate was 80% converted to isomaltulose and accompanying products, 88 g of crystalline product was obtained per 100 g of sucrose substrate and the productivity of the column was 0.30 tonnes of dry crystalline product/column volume/yr.

During operational use, the viable cell count of the immobilized cells decreased rapidly: the viable cell count reached zero after about 500 h operational use. After this period no viable cells remained and no involution forms of the cells were seen. Despite the comparatively rapid loss of viability, the isomaltulose synthesising activity of the immobilized cells decayed independently and much more slowly, with a half-life of 354 days.

This finding shows that viable cells are not required for isomaltulose formation, and that there is probably a single stable enzyme which converts the sucrose to isomaltulose and which does not require recycling of cofactors or continuous regeneration of energy sources. This hypothesis was confirmed when 0.1 g/l of chloramphenicol, which inhibits protein synthesis, was included in the 55% (w/v) sucrose used as substrate. The isomaltulose-synthesising activity was unaffected but no cell division took place, even when nutrients were supplied.

De novo growth of the Erwinia cells in situ could be induced by supplying nutrients in the form of fresh sterile medium, even after the cells had been used continuously in the column for a long period, such that the isomaltulose synthesing activity had fallen to a small fraction of its original value. In these experiments, medium was pumped up the column at 0.01 ecv/h. Considerable quantities of $CO_2$ were emitted by the immobilized cell pellets, the pH of the spent medium eluted from the column fell to pH 4.4, there were increases in the viable cell numbers both in the pellets and in the spent medium, and nitrogen analysis of both the spent medium and the cell pellets showed that cell growth had taken place. Most importantly, after switching back to 55% sucrose as substrate, the isomaltulose forming activity of the pellets was increased, in some cases to levels greater than the original activity. We have no evidence for induction of enzyme in the original cell, but did find that regeneration was entirely due to cell growth. The degree of reactivation of the activity of the pellets was proportional to the number of viable cells remaining immediately before nutrients were supplied, and no reactivation was obtained with the pellets which had been used for very long periods such that all the entrapped cells had become non-viable (500 h).

After operational use of the regenerated cells for a further period, the activity of the column could be reactivated in a like manner for at least 3 cycles. The ability to regenerate immobilized cell columns enables the stability of the column to be theoretically infinite and allows the age of the immobilized cells to be independent of the throughput of substrate.

Rather than supply nutrients intermittently after the pellets had been used for a period, the growth medium could be supplied to the column immediately after immobilization. In these experiments, a slow growth of Erwinia cells occurred in situ. When a 1% (ww/v) cell pellet inoculum was immobilized, a 30-fold increase in viable cell numbers was obtained, the cells growing with a doubling time of 64 h, before the experiment had to be terminated due to a gross weakening of the alginate gel structure. When cells were used in this mode, with frequent regeneration of activity by allowing cell growth to occur, the intrinsic stability of the enzyme system was less than when no cell growth occurred. Thus it appears that enzyme is much more stable when the cell is in a pseudo-resting or maintenance state than when allowed to divide.

EXAMPLE 2

The basic procedure of Example 1 was used with the additional step that the harvested cells of *Erwinia rhapontici* were disrupted by ball-milling for 90 minutes at 8° C. before immobilization. The initial activity of the pellets was similar to that when using whole cells as in Example 1 but the half-life was about 170 days.

EXAMPLE 3

The procedure of Example 1 was followed using other strains of isomaltulose-producing micro-organisms, namely *Erwinia rhapontici* (NCPPB 1578, 139 and 1739, and ATCC 29284), *Erwinia caratovora var atroseptica* NCPPB 139, *Erwinia dissolvens* (NCPPB 1862 and 2209), *Protaminobacter rubrum* (CBS 574, 77), *Serratia merscesens* (NCIB 8285) and *Serratia plymuthica* (ATCC 15928). The specificities, activities and stabilities of the immobilized strains were measured. Then by also taking in to account the pathogencity of the microorganisms and any tendency to produce polymer or pigment, the test strains (including that of Example 1) were assessed for the suitability in the process of Example 1. The assessments were as shown in the following Table 2.

TABLE 2

| Strain Suitability | |
|---|---|
| Strain | Suitability |
| E. rhapontici NCPPB 1578 | +++++ |
| E. rhapontici NCPPB 139 | +++++ |
| E. rhapontici NCPPB 1739 | +++++ |
| E. rhapontici ATCC 29284 | ++++ |
| E. carotovora var atroseptica NCPPB 139 | +++ |
| E. dissolvens NCPPB 1862 | ++ |
| e. dissolvens NCPPB 2209 | ++ |
| Serratia plymuthica ATCC 15928 | + |
| Serratia marscenscens NCIB 8285 | + |
| Protaminobacter rubrum CBS 574.77 | + |

EXAMPLE 4

The procedure described in Example 1 was followed using various sucrose concentrations of 12.5 to 60% (w/v). The activities and half-lives were measured for an initial percentage conversion to products of 4%, and the results are given in the following Table 3.

TABLE 3

| Sucrose Concentration | | |
|---|---|---|
| Sucrose Concentration (%, w/v) | Activity g product/ wet cells/h | Half-life (h) |
| 12.5 | 0.4 | 47 |
| 25 | 0.7 | 200 |
| 35 | 1.18 | 415 |
| 45 | 1.17 | 650 |
| 55 | 0.82 | 4000 |
| 60 | 0.31 | 1935 |

The variation in sucrose concentration of the substrate has a number of important effects on the performance of the immobilized columns. Firstly, the sucrose concentration affects the activity of the immobilized cells, with concentrations in excess of around 40% (w/v) proving inhibitory. On the other hand, it was surprising that the stability (ie half-life) of the immobilized cells increased very markedly as the sucrose concentration rose above the concentrations used by previous workers. The increase in stability of the immobilized cells with increased sucrose concentration more than compensates for any decrease in activity, and so the productivity of the column rose with increase in sucrose concentration.

The equilibrium products: sucrose was also found to vary markedly with the sucrose concentration used as substrate, the highest equilibrium values being obtained when 55% (w/v) sucrose was used. Thus, with 55% sucrose the products:sucrose equilibrium ratio was about 13.2, corresponding to 93% conversion to products.

EXAMPLE 5

The procedure described in Example 1 was followed using cells of *Erwinia rhapontici* NCPPB 1578 immobilized by other immobilization techniques as particularized earlier in this specification. The activities and half-lives were as shown in the following Table 4.

TABLE 4

| Immobilization technique | | |
|---|---|---|
| Immobilization Technique | Activity (g Product/ g wet cells/h) | Half-life (hours). |
| Calcium alginate | 0.325 | 8,500 |
| DEAE cellulose | 0.583 | 400 |
| Polyacrylamide | 0.13 | 570 |
| Glutaraldehyde aggregated cells | 0.153 | 40 |
| K-carrageenan-locust bean gum | 0.263 | 37.5 |
| Bone char | 0.01 | 25 |
| Agar | 0.34 | 27 |
| Xanthan-locust bean gum | 0.10 | 8 |

EXAMPLE 6

N methyl-N'-nitro-N-nitrosoguanidine (100 µg/ml) was dissolved in 25 ml of 0.10 M citrate buffer pH 6.0 by incubating in a water bath at 37° C. for 20 min. This solution was then added to 50 ml of filtered nutrient broth containing approximately 1 g of freshly harvested *E. rhapontici* NCPPB 1578 cells. The cells were then incubated for 30 min at 37° C. in a water bath, harvested and suspended in the 4% sucrose medium (Table 1) overnight at 4° C. Aliquots (0.1 ml) were plated out on 1.5% (w/v) agar plates containing sucrose 4% (w/v), tryptone 0.4%, (w/v) and peptone 1% (w/v) adjusted to pH 7.0 and incubated for 48 h at 30° C. Individual colonies were then inoculated into shake flasks and cultivated for 48 h at 30° C. while shaking at 120 rpm, then harvested and the cells assayed and analysed. The mutant strains were typically less specific than the original cells, though isomaltulose was produced.

EXAMPLE 7

The procedures described in Example 1 were carried out using alginate gel containing entrapped NCPPB 1578 cells which had been gelled either in a block and cut into fragments, or gelled in a continuous strand and used either wound on a rod or cut into segments. When used in columns, these immobilized cells showed no noticeable difference in activity or stability when compared with cells immobilized in spherical pellets.

EXAMPLE 8

Example 3 indicates that the strains of *E. rhapontici* were particularly suitable. A further comparison was carried out under standardized conditions using each of three *E. rhaponcici* strains immobilized in calcium alginate. The results were as follows in Table 5:

TABLE 5

| Strain of E. rhapontici | Initial Conversion (%) | Activity (g product/ g cells/h) | Half-life (h) | Productivity (kg. product/ liter/ column/vol. 1000h) |
|---|---|---|---|---|
| NCPPB 1578 | 52.4 | 0.441 | 1507 | 59.52 |
| NCPPB 139 | 54.4 | 0.389 | 1877 | 52.53 |
| NCPPB 1739 | 56.6 | 0.354 | 1840 | 47.77 |

EXAMPLE 9

The enzyme system responsible for the conversion of sucrose into isomaltulose was solvent extracted from cells of *Erwinia rhapontici* NCPPB 1578 using four different techniques, namely Mickle shaking, osmotic shock, sonication or detergent treatment.

For Mickle shaking, 2 g aliquots of freshly harvested cells were shaked with 2 g dry sand and 2 ml distilled water for 20 minutes at room temperature using a Mickle shaker set for maximum gyrorotatory oscillation.

For the osmotic shock technique, 1.5 g aliquots of the cells were suspended in 10 ml of deionized water for 30 minutes at 1° C.

For sonication, 2 g aliquots of cells were suspended in 15 ml of deionized water and sonicated for 30 minutes using a sonicator with a tip diameter of 2.5 cm.

For detergent treatment, 0.5 g (v/v) aqueous Triton X-100 solution for 3 hours was used. (Triton X-100 is a Registered Trade Mark).

After each respective treatment, the resultant suspension was centrifuged at 17000 g for 30 minutes at 30° C.

The cells or dell debris and the supernatant were then separately immobilized in pellets of calcium alginate, using the general procedure of Example 1.

The pellets were then assayed against 55% (w/v) sucrose for isomaltulose synthesising activity, giving the results shown in Table 6 where 'IM' stands for isomaltulose and accompanying products.

extract having an activity of 0.253 g products/ml/h and a specific activity of 0.0844 g product/mg protein/g. Moreover polyacrylamide gel electrophoresis showed only ten protein bands. The comparatively high purity of this enzyme extract is probably because the cells were not disrupted by the osmotic shock.

From our results, it appears that the enzyme system is membrane associated and/or compartmentalized in the cell, the most likely location being the periplasmic space, especially as osmotic shocking is the best method of extraction and because we have also found that the periplasmic space marker enzymes such as acid phosphatase were co-extracted by the osmotic shock treatment.

Considering in Table 6 the initial activities of the osmotically shocked, Mickle-shaken and untreated cells, the disrupted cells had the greatest activity. This is probably due to the removal of the diffusional restriction on substrate transfer caused by an intact cell wall and membrane. However there was no significant difference in the activities of the osmotically shocked, non-viable cells and fresh viable cells demonstrating that no active transport system for the uptake of sucrose into the cell is in operation, as such a system would be dependent on the integrated metabolism of the whole cell and so would be expected to be lost when the cells were osmotically shocked.

Further work on the cell-free enzyme extract obtained by osmotic shocking showed that it had a pH optimum of pH 7.0, a temperature optimum of 30° C. and was maximally active in 35% (w/v) sucrose solution. That the substrate optimum for the soluble enzyme system is less than that (55%) of the free cells or immobilized cells is not surprising and presumably reflects a modification of the intrinsic properties of the enzyme system imposed by its periplasmic location. When the Mickle-shaken extracted enzyme system was used on 55% (w/v) sucrose, the immobilized enzyme had an initial activity of 0.0067 g product/g pellets/h and a half life of 620 h while achieving an initial degree of conversion of 81.5%.

Using universally and specifically labelled sucrose, fructose and glucose as substrate for the extracted enzyme system, we found the system to include a sucrose specific glucotransferase. The enzyme is also specific for the acceptor moiety as only the fructose derived from sucrose, and not exogenously added fructose, glu-

TABLE 6

| | Activity of original cell (g IM/gww/h) | Activity of cell degris (g IM/gww original cells/h) | Activity of supernatant | | Protein conc. of extract (mg/ml) | Specific Activity (g IM/mg protein/h) |
|---|---|---|---|---|---|---|
| | | | (g IM/gww orig. cells/h) | (g IM/ml extract/h) | | |
| Mickle shaken | 0.63 | 0.567 | 0.094 | 0.094 | 32.6 | 0.0029 |
| Osmotically shocked | 0.70 | 0.465 | 0.038 | 0.253 | 3.0 | 0.0844 |
| Sonicated | 0.63 | 0.514 | 0.042 | 0.042 | 14.9 | 0.0028 |
| Triton X-100 treated | 1.16 | — | 0.046 | 0.92 | — | — |

From the results given in Table 6, it will be seen that Mickle-shaking released into the supernatant about 5% of the activity of the cells, all of the remaining activity being associated with the cell debris. The soluble enzyme extract, ie the supernatant, had an activity of 0.094 g products/ml/h, a specific activity of 0.0029 g products/mg protein/h and contained twelve different protein bands when analysed by polyacrylamide gel electrophoresis.

The enzyme system was extracted more efficiently by the osmotic shocking of the cells. By this method, approximately 9% of the cells activity was extracted, the cose or glucose and fructose is available for incorporation into isomaltulose. Presumably the glucose and fructose derived from sucrose is 'activated' in some way; for instance, it may exist in a sterically more favourable environment. The enzyme system did not give a purer product than was obtained using the whole cells.

We claim:

1. A process for the production of isomaltulose, which process consists essentially of immobilizing by entrapment within a calcium alginate gel at least the isomaltulose-forming enzyme system of an isomaltulose-forming micro-organism of the genus Erwinia and then contacting the immobilized enzyme system with a sucrose solution containing at least 30% (w/v) of sucrose to convert at least part of the sucrose to isomaltulose.

2. The process of claim 1, wherein said enzyme system is immobilized as whole cells of said isomaltulose-forming micro-organism.

3. The process of claim 1, wherein said enzyme system is immobilized as a solvent extract of whole or disrupted cells of said isomaltulose-forming micro-organism.

4. The process of claim 1, wherein said micro-organism is of the species *E. rhapontici*.

5. The process of claim 7, wherein said micro-organism is of the strain *E. rhapontici* NCPPB 1578.

6. The process of claim 1, wherein said sucrose solution contains at least 40% (w/v) of sucrose.

7. The process of claim 6, wherein said sucrose solution contains about 55% (w/v) of sucrose.

8. The process of claim 1, wherein from 70 to 95% of said sucrose is converted to isomaltulose.

9. The process of claim 1, which includes the further step of purifying isomaltulose from the resulting solution.

10. The process of claim 9, wherein the isomaltulose is crystallized from the resulting solution to yield crystals containing 90% or more of isomaltulose.

11. The process of claim 1, calcium alginate gel, the isomaltulose-forming micro-organism, the immobilized enzyme system is contacted with a sucrose solution of pH 5–9 containing at least 40% (w/v) of sucrose at 15°–40° C. for a length of time sufficient to convert 80–90% of said sucrose to isomaltulose.

12. The process of claim 11, wherein said sucrose solution is nutritionally deficient lacking at least one nutrient required for growth of the isomaltulose forming micro-organism.

* * * * *